(12) United States Patent
Ragg

(10) Patent No.: US 11,311,635 B2
(45) Date of Patent: Apr. 26, 2022

(54) ULTRASONIC COUPLANT SPRAY

(75) Inventor: Johann Christof Ragg, Berlin (DE)

(73) Assignee: ANGIOCLINIC AG, Frauenfeld (CH)

( * ) Notice: Subject to any disclaimer, the term of this patent is extended or adjusted under 35 U.S.C. 154(b) by 591 days.

(21) Appl. No.: 14/128,341

(22) PCT Filed: Jun. 21, 2012

(86) PCT No.: PCT/EP2012/062023
§ 371 (c)(1),
(2), (4) Date: Feb. 24, 2014

(87) PCT Pub. No.: WO2013/004518
PCT Pub. Date: Jan. 10, 2013

(65) Prior Publication Data
US 2014/0200450 A1  Jul. 17, 2014

(30) Foreign Application Priority Data
Jul. 1, 2011  (EP) .................................... 11172307

(51) Int. Cl.
*A61K 49/22* (2006.01)
*A61B 8/08* (2006.01)

(52) U.S. Cl.
CPC .............. *A61K 49/226* (2013.01); *A61B 8/48* (2013.01)

(58) Field of Classification Search
CPC ...... A61K 49/04; A61K 49/10; A61K 31/723; A61K 31/047; A61K 8/63; A61K 9/0095
USPC ........................................ 424/9.1, 9.4, 9.453
See application file for complete search history.

(56) References Cited

U.S. PATENT DOCUMENTS

| 4,774,017 A * | 9/1988 | Seibert .................. A61K 47/10 510/405 |
| 5,398,290 A * | 3/1995 | Brethour ................ A01K 29/00 128/925 |
| 6,485,575 B2 * | 11/2002 | Yuan ........................ A21D 2/16 106/162.81 |
| 2006/0019858 A1 * | 1/2006 | Kruse .................... A61K 8/466 510/424 |
| 2006/0246111 A1 * | 11/2006 | Smith .................. A61K 49/226 424/427 |
| 2008/0178899 A1 * | 7/2008 | Moenks ................. A61K 8/046 132/203 |

(Continued)

FOREIGN PATENT DOCUMENTS

| DE | 44 34 626 | 4/1996 |
| DE | 10 2008 014 467 | 9/2009 |
| DE | 102008014467 A1 * | 9/2009 ........... A61K 49/222 |

(Continued)

OTHER PUBLICATIONS

Bete Spray Dry Manual, 2005 Bete Fog Nozzle Inc., 2005.*
(Continued)

*Primary Examiner* — Melissa S Mercier
(74) *Attorney, Agent, or Firm* — Ballard Spahr LLP (57) ABSTRACT

The application discloses the use of an aqueous composition comprising a thickener, and an antiseptic compound or a pharmaceutical acceptable salt thereof as an ultrasonic couplant spray. An ultrasonic couplant spray comprising starch, and an antiseptic compound or a pharmaceutical acceptable salt thereof is also disclosed. Furthermore, the present application relates to a kit comprising a composition according to the present application and spray device.

13 Claims, 5 Drawing Sheets

(56) References Cited

U.S. PATENT DOCUMENTS

2009/0170744 A1* 7/2009 Meine ................ C11D 3/0063
                                                    510/302
2011/0125026 A1* 5/2011 Neto ....................... A61B 8/06
                                                    600/463

FOREIGN PATENT DOCUMENTS

| DE | 10 2009 007 152      | 8/2010 |              |
|----|----------------------|--------|--------------|
| DE | 102009007152 A1 *    | 8/2010 | ...... A61K 31/167 |
| EP | 2 415 487            | 2/2012 |              |
| WO | WO 03/018067         | 3/2003 |              |
| WO | WO 2003018067   *    | 3/2003 |              |
| WO | WO 2009/009064       | 1/2009 |              |

OTHER PUBLICATIONS

Murao et al., Isolation of Amylase Inhibitor-producing Microorganism, Agric. Biol. Chem., 41 (6), 919-924, 1977.*

Parikh et al., Ultrasound-accelerated Thrombolysis for the Treatment of Deep Vein Thrombosis: Initial Clinical Experience; J Vasc Interv Radiol 2008; 19:521-528.*

"Potassium Sorbate", PAN Pesticides Datsbase—Chemicals, 2011, XP002662751, Retrieved from the Internet: URL:http://www.pesticideinfo.org/Details_Chemical.jsp?Rec_Id=PC34447 [retrieved on Nov. 4, 2011.

International Search Report dated Sep. 18, 2012 in International Patent Application No. PCT/EP2012/062023.

* cited by examiner

ULTRASONIC COUPLANT SPRAY

This application is a National Stage of PCT/EP2012/062023, filed Jun. 21, 2012, which claims priority to European Patent Application No. 11172307.8, filed Jul. 1, 2011, the disclosures of each of which are incorporated herein by reference in its entirety.

FIELD OF THE INVENTION

The present invention relates to the field of pharmaceutical compositions and medical devices. Particularly, the present invention relates to a novel ultrasonic couplant composition for use in interventional applications.

BACKGROUND OF THE INVENTION

Diagnostic sonography (ultrasonography) is an ultrasound-based diagnostic imaging technique used to visualize subcutaneous body structures including internal organs, glands, fatty and connective (issue, blood vessels, muscles, joints and tendons, for possible pathology or lesions. Obstetric sonography is commonly used during pregnancy and is widely recognized by the public. Beside diagnostic procedures, it is possible to perform ultrasound-guided therapeutic procedures, using ultrasound as a real-time imaging during interventional procedures (for instance tissue biopsies, drainage of fluid collections, or access to blood vessels). Sonographers typically use a hand-held probe (called a transducer) that is placed directly on and moved over the patient. As any air between skin and transducer works as a resistance to ultrasound propagation, it has to be replaced by sound-conducting media. In the ideal case, these transducer couplants are sound-transparent (no or minimal echoes), without reactions to the skin (allergy, inflammation) and with good gliding properties to facilitate the movement on the skin.

For interventional therapies, the skin has to be punctured in one or several locations, which is usually performed under sterile conditions, using sterile tools after carefully disinfecting the skin two or three times. If the area is to be controlled by sonography, the use of couplants will raise the danger of infection, as microbial pathogens may be spread from pores to the couplant and vice versa. Ultrasonic couplants that are used nowadays do not provide any disinfection.

Disinfectant fluids or gels are not suitable for use in ultrasonography, as they do not provide sufficient contact, allow only poor gliding, dry off too fast or are aggressive to the sensitive transducer surface.

Hence, it is one object of the present invention to provide for compositions with enhanced properties with respect to disinfection and ultrasonographic properties, such as coupling but also medical applicability and patient comfort.

DESCRIPTION OF THE INVENTION

The inventors unexpectedly found that an aqueous composition comprising a thickener and an antiseptic compound when applied as a spray shows dramatically increased antiseptic properties while being well suited as an ultrasonic couplant. Further, the inventors have found that healing is accelerated.

The thickener may be hyettelose (hydroxyethyl cellulose), arrowroot, cornstarch, katakuri starch, potato starch, sago, tapioca, vegetable gums, alginin, guar gum, locust bean gum, and xanthan gum, collagen, egg whites, furcellaran, gelatin, agar, carrageenan or sodium pyrophosphate.

Different thickeners may be more or less suitable in the given application due to differences in clarity, and their responses to chemical and physical conditions.

The thickener may be a gelling agent such as natural gums, starches, pectins or agar-agar gelatine.

Examples for thickeners are: Alginic acid (E400), sodium alginate (E401), potassium alginate (E402), ammonium alginate (E403), calcium alginate (E404), polysaccharides from brown algae, Agar (E406, a polysaccharide obtained from red algaes), Carrageenan (E407, a polysaccharide obtained from red seaweeds), Locust bean gum (E410, a natural gum polysaccharide from the seeds of the Carob tree), Pectin (E440, a polysaccharide obtained from apple or citrus-fruit) or Gelatine (E441, made by partial hydrolysis of animal collagen).

Although starch has turned out to be very good for the present application other thickeners may be used as well. Organic polymers herein are also thickeners.

Hence, the present invention relates to the use of a composition comprising starch, and an antiseptic compound or a pharmaceutical acceptable salt thereof as an ultrasonic couplant spray.

The invention also relates to a kit comprising a spray device and an ultrasonic couplant composition comprising and starch and an antiseptic compound.

The present invention, furthermore, relates to an ultrasonic couplant spray comprising starch, and an antiseptic compound or a pharmaceutical acceptable salt thereof.

The invention also relates to the use of an ultrasonic couplant spray or a kit according to the present invention in sonography.

DETAILED DESCRIPTION OF THE INVENTION

The present invention relates to the use of an aqueous composition comprising a thickener and an antiseptic compound or a pharmaceutical acceptable salt thereof as an ultrasonic couplant spray.

In context with the present invention "starch" (or amylum) is a carbohydrate consisting of glucose units joined together by glycosidic bonds. It consists of two types of molecules: the linear and helical amylose and the branched amylopectin. The inventors unexpectedly found that the use of starch in the composition increases the viscosity and decreases evaporation. It has further been found that the time the antiseptic compound is in contact with the area to be investigated by ultrasound, e.g. for monitoring the interventional or surgical access to blood vessels, is increased by the composition according to the present invention due to the prevention of evaporation. This leads to enhanced properties of the use of the composition with respect to its antiseptic efficacy. Depending on the source, starch generally comprises 20% to 25% amylose and 75% to 80% amylopectin. The person skilled in the art is aware that starch may be provided coming from different sources and in different degrees of purity. Starch may be for example derived from different types of plants. Furthermore, the person skilled in the art knows that starch may be modified in order to adapt the properties, e.g. thickening of the ultrasonic couplant composition. Thus, in a preferred embodiment of the present invention the starch is selected from the group comprising corn starch, rice starch, wheat starch, potato starch, cassava starch and modified starch. The person of ordinary skills in the art knows modification of starch. He is furthermore aware of the modifications suited to reach the desired properties. A modified food starch is a starch that has been chemically modified to allow the starch to function properly under conditions frequently encountered during processing or storage, such as high heat, high shear, low pH, freeze/thaw and cooling. The modified starches are E-coded according to the International Numbering System for Food Additives (INS) (CODEX ALIMENTARIUS published in FNP 52 Add 9 (2001)). Thus, in a preferred embodiment of the present invention the modified starch is selected from the group consisting of acid-treated starch (1401), alkaline-treated starch (1402), bleached starch (1403), oxidized starch (1404), starches, enzyme-treated (1405), monostarch phosphate (1410), distarch phosphate (1412), phosphated distarch phosphate (1413), acetylated distarch phosphate (1414), starch acetate (1420), acetylated distarch adipate (1422), hydroxypropyl starch (1440), hydroxypropyl distarch phosphate (1442), hydroxypropyl distarch glycerol (1443), starch sodium octenyl succinate (1450), and acetylated oxidized starch (1451) (the respective INS numbers are given in brackets). However, in one embodiment the starch is corn starch. In a further embodiment mixtures of two or more of the above mentioned starches are comprised in the ultrasonic couplant composition according to the present invention.

The starch in context with the present invention serves as a thickening agent and lubricant. The person skilled in the art knows that the degree of thickening, i.e. the viscosity of the ultrasonic couplant composition may be varied by varying the concentration of the thickening agent, i.e. the starch. He will for example increase the starch concentration of the composition in order to increase the viscosity; accordingly, he will decrease the concentration if a composition of lower viscosity is desirable. However, the viscosity has to be in a range allowing spraying of the composition. The inventors unexpectedly found that a composition comprising 2% to 20% starch is well suited for spraying. Hence, in a preferred embodiment of the present invention starch of the ultrasonic couplant composition has a concentration of 2% to 20%, preferably 4% to 15%, more preferably 6% to 10%.

For the present invention, the term "antiseptic" is meant to include but not be limited to the following: antimicrobial agents, antibiotics, chemotherapeutic agents, any antiseptics, antiviral agents, virucidal agents, bactericidal agents, antifungal agents, antiparasitic agents, and the like. The words "antiseptic", "disinfectant", and "germicide" all connote an agent which can kill microbes or infectious pathogens upon contact and thousands of chemical compounds are known which have antiseptic properties (For some examples see Remingtons Pharmaceutical Sciences: 1985, 1990 and Harvey, 1985). In a preferred embodiment of the present invention the antiseptic compound is bactericidal and/or fungicidal and/or virucidal; preferably the antiseptic compound is bactericidal and fungicidal or bactericidal and virucidal or fungicidal and virucidal. However, it is especially preferred that the antiseptic compound is bactericidal and fungicidal and virucidal.

Furthermore, more than one antiseptic compound may be comprised in the ultrasonic couplant composition according to the present invention. In a further embodiment the ultrasonic couplant comprises at least two antiseptic compounds, preferably at least three antiseptic compounds, more preferably at least four antiseptic compounds are comprised in the ultrasonic couplant according to the present invention. The antiseptic compounds may be chosen independently from the antiseptic compounds as outlined herein.

The antiseptic compound includes iodine, an iodine complex, chlorhexidine, chlorhexidine salts, or combinations thereof. Preferred iodine complexes may include iodophors, e.g., povidone-iodine USP. Preferred chlorhexidine salts may include, e.g., chlorhexidine digluconate and chlorhexidine diacetate. Other suitable antiseptic compounds may include parachlorometaxylenol (PCMX), triclosan, hexachlorophene, fatty acid monoesters of glycerine and propylene glycol such as glycerol monolaurate, glycerol monocaprylate, glycerol monocaprate, propylene glycol monolaurate, propylene glycol monocaprylate, propylene glycol moncaprate, phenols, surfactants, and polymers that include a ($C_{12}$-$C_{22}$) hydrophobic and a quaternary ammonium group, polyquaternary amines such as polyhexamethylene biguanide as well as those described in U.S. Pat. Nos. 6,440,405, 5,408,022 and 5,084,096, quaternary ammonium silanes, silver, silver salts (such as silver chloride), silver oxide and silver sulfadiazine, methyl, ethyl, propyl and butyl parabens, octenidene, peroxides (e.g., hydrogen peroxide and benzoyl peroxide), and the like, as well as combinations thereof.

Interestingly, it has been found by the inventors that quaternary ammonium compounds are especially well suited for the ultrasonic couplant according to the present invention. Thus, in a preferred embodiment the antiseptic compound is a quaternary ammonium compound or a pharmaceutically acceptable salt thereof, more preferably the antiseptic compound is selected from the group comprising octenidin hydrochloride, benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide, povidone iodine, elemental iodine, sodium iodide, potassium iodide, sodium hypochlorite, nonoxynol-9, and chlorhexidine gluconate.

The phrase "pharmaceutically acceptable salt(s)", as used herein, means those salts of compounds of the invention that are safe and effective for topical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminium, calcium, lithium, magnesium, potassium, sodium, zinc, ammonium and diethanolamine salts. For a review on pharmaceutically acceptable salts see BERGE ET AL., 66 J. PHARM. SCI. 1-19 (1977), incorporated herein by reference.

The inventors interestingly found that the properties of the composition can be further modified if anaesthetic compounds are added.

When such a compound is used, the area to be investigated by ultrasound can be anaesthetized. Hence, in one embodiment of the present invention the composition further comprises (i) a fast-acting local anaesthetic compound or a pharmaceutical acceptable salt thereof; and/or (ii) a local anaesthetic compound with long lasting anaesthetic effect or a pharmaceutical acceptable salt thereof.

The composition of the present invention in one embodiment comprises local anaesthetic compounds. A local anaesthetic compound is a drug that causes reversible local anaesthesia and a loss of nociception. When it is used on specific nerve pathways (nerve block), effects such as analgesia (loss of pain sensation) and paralysis (loss of muscle power) can be achieved.

Local anaesthetics belong to one of three classes: amino amide, amino ester and amino amide ester local anaesthetics. Synthetic local anaesthetics are structurally related to cocaine. Most of the local anaesthetics share common structural features. They comprise a lipophilic group and a hydrophilic group connected by an alkyl chain differing in length, wherein the alkyl chain is bond to the lipophilic group through an ester bond or an amide bond or an ester and amide bond. Accordingly the local anaesthetics are grouped into amide-type local anaesthetic drug, amino ester-type local anaesthetic drug, and amino amide ester-type local anaesthetic drug (http://www.deutscher-apotheker-verlag.de/uploads/tx_crondavtitel/datei-datei/9783804725027_p.pdf).

In a preferred embodiment the fast-acting anaesthetic compound and the local anaesthetic compound with long lasting anaesthetic effect are independently selected from the group comprising amino amide-type local anaesthetic drug, amino ester-type local anaesthetic drug, and amino amide ester-type local anaesthetic drug.

Local anaesthetics vary in their pharmacological properties, i.e. their period of anaesthetic effect and/or the period between application of the compound and initiation of the anaesthesia. In context of the present invention it is desirable that the ultrasonic couplant composition provides both, a rapid initiation of anaesthesia as well as a long lasting anaesthetic effect. The problem is solved by the present invention by providing an ultrasonic couplant composition comprising a fast-acting anaesthetic compound and the local anaesthetic compound with long lasting anaesthetic effect.

In context of the present invention a fast-acting anaesthetic compound initiates local anaesthesia within 10 s to 1 h after application of the compound on the skin of a subject, preferably within 30 s to 30 min after application, more preferably within 1 min to 15 min after application.

In context of the present invention a local anaesthetic compound has a long lasting anaesthetic effect if the local anaesthesia lasts for 1 h to 24 h after application of the compound on the skin of a subject, preferably for 2 h to 15 h, more preferably 4 h to 6 h. Also preferred are anaesthetic compounds having a long lasting anaesthetic effect which causes a local anaesthesia for 4 h to 5 h.

The person skilled in the art is aware of local anaesthetic compounds having the desired properties. However, in a preferred embodiment of the present invention the fast-acting anaesthetic compound is selected from the group comprising lidocaine, mepivacaine, prilocaine, articaine, etidocaine, benzocaine, and 2-chlor procaine. In a further preferred embodiment of the present invention the local anaesthetic compound with long lasting anaesthetic effect is selected from the group consisting of bupivacaine, ropivacaine, procaine and tetracaine.

The person skilled in the art is furthermore able to determine the desired concentration of the fast-acting anaesthetic compound. For example a high concentration may be desirable if the ultrasonic couplant is used at sensitive parts of the body in order to increase the anaesthetic effect. However, in a preferred embodiment of the ultrasonic couplant composition the fast-acting anaesthetic compound has a concentration of 1 mg/g to 100 mg/g, preferably 2 mg/g to 50 mg/g, more preferably 3 mg/g to 20 mg/g, even more preferably 4 mg/g to 10 mg/g. In a further preferred embodiment of the ultrasonic couplant composition according to the present invention the local anaesthetic compound with long lasting anaesthetic effect has a concentration of 1 mg/g to 100 mg/g, preferably 2 mg/g to 50 mg/g, more preferably 3 mg/g to 20 mg/g, even more preferably 4 mg/g to 10 mg/g.

Starch is used for the ultrasonic couplant composition. Starch is easily biodegradable. This increases the danger of contamination of the composition with microorganisms like fungi and/or bacteria. This problem is solved by the provision of an ultrasonic couplant composition comprising at least one preservative. Thus, in a preferred embodiment the ultrasonic couplant further comprises preservative compounds. A preservative is a naturally occurring or synthetic substance that is added to products such as pharmaceuticals to prevent decomposition by microbial growth or by undesirable chemical changes. Suited preservatives are known by those of ordinary skill in the art. In a preferred embodiment the preservative compound is bactericidal and fungicidal. In a further preferred embodiment of the present invention the preservative compound is, e.g. phenoxyethanol.

In yet a further embodiment the ultrasonic couplant composition according to the present invention comprises at least two preservative compounds, preferably at least three, more preferably at least four preservative compounds. If more than one preservative compound is comprised in the composition, the preservative compounds may be chosen independently from the preservative compounds as outlined herein. It is also preferred that the preservative compound is selected from the group comprising antioxidants, bactericidal compounds, fungicidal compounds, potassium sorbate, sodium benzoate, sodium methyl paraben, citric acid.

The ultrasonic couplant composition according to the present invention comprises starch as a thickening agent. Starch is insoluble in aqueous solution but forms a hydrocolloid after heating. However, it has been found that the ultrasonic couplant composition comprising starch tends to form precipitates of starch. The inventors unexpectedly found that the problem of the precipitation of starch may be solved by adding fatty substances and/or emulsifying agents and/or starch degrading enzymes to the composition. Thus, in a preferred embodiment the ultrasonic couplant further comprises at least one compound selected from the group comprising fats, emulsifying agents, starch degrading enzymes.

The fatty substances to be used in the composition according to the invention may include vegetal oils (such as almond, jojoba and avocado oil), mineral oils, oils of animal origin (such as lanoline), synthetic oil (esters such as isopropyl myristate, decyl oleate, isopropyl palmitate), silicone oils (such as cyclomethicone and dimethicone) and fluorinated oils. Fatty alcohols and acids and waxes (such as bee wax and rice wax) may also be used. In a preferred embodiment of the present invention the ultrasonic couplant composition comprises at least two fatty substances, preferably at least three fatty substances, more preferably at least four fatty substances. If more than one fatty substance is comprised in the ultrasonic couplant composition, the fatty substances may be chosen independently from the fatty substances as outlined herein.

The emulsifying agents to be used in the composition may include polyglycerol fatty acid esters, saccharose fatty acid esters, sorbitan fatty acid esters, ethoxylated sorbitan fatty acid esters, ethers of fatty alcohols and PEG, glycerol fatty acid others, alkyl sulfates, alkyl ether sulfates, alkyl phosphates, alkyl polyglucosides and, e.g. dimethicone co-polyols. Examples of ethoxylated emulsifyers are steareth-2 and steareth-21, while examples of glucoside-based emulsifyers are cetearyl glucoside and arachidyl glucoside. In a preferred embodiment of the present invention the ultrasonic couplant composition comprises at least two emulsifying agents, preferably at least three emulsifying agents, more preferably at least four emulsifying agents. If more than one emulsifying agents is comprised in the ultrasonic couplant composition, the emulsifying agents may be chosen independently from the emulsifying agents as outlined herein.

Starch degrading enzymes are known by those of ordinary skills in the art. Starch degrading enzymes are enzymes that break down or hydrolyze starch. Examples of such enzymes are α- and β-amylases. α-amylases are found in plants and in animals. However, α-amylase in context with the present invention may be of different sources including plants and animals. Furthermore also α-amylases which have been recombinantly expressed in microorganisms, such as bacteria and fungi, are encompassed by the present invention. In a further embodiment of the present invention the starch degrading enzyme is a β-amylase and/or α-amylases, preferably an α-amylase. β-amylase cuts starch into maltose units. The person skilled in the art knows how to purify α-amylases and/or β-amylase from natural sources, i.e. plants or animals. He furthermore knows methods for recombinantly expressing α-amylase and/or β-amylase in microorganism, e.g. *Escherichia coli*, by using for example expression vectors.

The inventors unexpectedly found that the use of a composition comprising starch and an antiseptic compound as an ultrasonic couplant spray provides for improvements with respect to disinfection of the area to be investigated. Hence, the present invention relates to a kit comprising a spray device and an ultrasonic couplant composition comprising starch and an antiseptic compound.

The gel becomes liquefied and may be used as a spray according to the invention when it is mechanically sheared, e.g. with a shear bar or knives or mechanical treatment, or ultrasound energy. The inventors have used simple syringes and created the sprayable substance by pumping the gel back and forth between to syringes at a velocity of about between 100 to 300 km/h, preferably at between 120 km/h and 250 km/h. Thereafter the substance must rest for a while so that excess air bubbles can be extracted.

The present invention is directed to a composition being used as an ultrasonic couplant spray. An ultrasonic couplant spray herein is to be understood as the herein disclosed composition to be used as or in a spray device. A spray herein refers to a collection of liquid droplets or a spray device (spray bottle) depending on the context. Accordingly, in one instance, a spray is a dynamic collection of drops dispersed in a gas. A spray nozzle being part of a spray device is used to generate a spray. The two main uses of sprays are to distribute material over a cross-section and to generate liquid surface area.

The herein disclosed composition/ultrasonic couplant spray has the advantage that it does not form an aerosol. An aerosol is a colloid suspension of liquid droplets in a gas. An example is a cloud. Liquid droplets refer to small liquid droplets which remain in suspension in gas as a colloid or due to the motion of the gas. That means that the composition when used in a spray device is being distributed in small droplets though big enough to form an aerosol. Inventor hypothesizes that this behavior is due to the viscosity increase of the thickening agent leading to a droplet size that is too big for forming an aerosol.

The person skilled in the art will realize that the tendency to form an aerosol may increase with decreasing viscosity. Hence, liquid droplets may have an average diameter between 50 μm and 1000 μm, preferably between 50 μm and 500 μm, more preferably between 50 μm and 300 μm, more preferably between 50 μm and 200 μm, more preferably between 50 μm and 150 μm, most preferably between 50 μm and 100 μm. Alternatively, liquid droplets may have an average diameter between 70 μm and 1000 μm, preferably between 70 μm and 500 μm, more preferably between 70 μm and 300 μm, more preferably between 70 μm and 200 μm, more preferably between 100 μm and 300 μm, most preferably between 100 μm and 200 μm. Alternatively, the average diameter may be bigger than 30 μm, 40 μm, 50 μm, 60 μm, 70 μm, 80 μm, 90 μm, or 100 μm. It is clear that in all cases the average diameter shall be small enough to fall under the definition of a liquid droplet. For example, the average diameter may be below 1000 μm, preferably below 500 μm.

In s specific embodiment, the ultrasonic couplant spray comprises droplets exceeding an average diameter of 50 μm. In a further specific embodiment, the ultrasonic couplant spray consists of droplets exceeding an average diameter of 50 μm.

In other words, the invention relates to a collection of droplets, each droplet comprising a thickener, which is preferentially a starch, and an antiseptic compound or a pharmaceutical acceptable salt thereof. The average diameter of the droplets is preferably above 50 μm or has an average diameter as mentioned above.

In another specific embodiment, the spray device may be configured to spray droplets of the desired size, e.g. having an average diameter above 50 μm. One may readily understand that droplet size in a spray is not only determined by physicochemical parameters such as viscosity and density but also by physical characteristics of the spray device such as nozzle size, nozzle geometry and ejection velocity, i.e. pressure difference between the spray bottle and the environment.

The person skilled in the art will further recognize that the tendency to form an aerosol will depend on the density of the composition. However, this influence is minor because the density range of the herein described compositions is rather narrow and close to the value of water.

A "spray device" in context with the present invention is a system for dispensing liquid on the human body. One form of spray device for the application of liquids or compositions for skin treatment is a hand-held spray device. Usually these hand-held spray devices are comprised of disposable pressurized can spray applicators having a finger actuated spray valve and nozzle. Non-pressurized hand-held spray applicators are also available consisting of re-usable trigger-pump spray devices. These disposable and refillable trigger sprayers are held in one hand at less than a meter away from the skin to treat portions of the body. Container sizes for these types of sprayers are adapted to hold volumes of liquids adequate for the intended use. Suited spray devices are known by those of ordinary skills in the art.

A further advantage of the spray over the gel is that the amount of spray required compared to the known gel is much smaller. Cleaning and post diagnostic and operative procedures become much easier that way. Compared to disinfectant sprays, the invention will not produce inhalable aerosols which could harm the pulmonary tract.

As used herein, a kit is a packaged combination optionally including instructions for use of the combination and/or other reactions and components for such use.

The invention is further directed to a kit comprising a spray device and an ultrasonic couplant composition comprising a thickener, which is preferentially a starch and an antiseptic compound. The spray device may be pre-filled with the ultrasonic couplant, or the spray device and the ultrasonic couplant are separated from each other, i.e. the spray device may be not filled with the ultrasonic couplant.

In a preferred embodiment of the present invention the kit further comprises a device and/or substance for marking the skin. As the composition according to the present invention comprises starch, it is easily markable using iodine comprising agents. Hence, in a further embodiment of the present invention the device for marking the skin of a subject comprises iodine. Devices and substances for marking the skin of a subject are known by those skilled in the art. They may, for example, be selected from the group consisting of marker pens, swabs and marking liquids comprising iodine. Liquids comprising iodine are also known in the art and may e.g. be selected from the group comprising Braunol® and, e.g. povidone-iodine (PVP-I) comprising substances which is a stable chemical complex of polyvinylpyrrolidone (povidone, PVP) and elemental iodine. It contains from 9.0% to 12.0% available iodine, calculated on a dry basis.

In one embodiment the marker pen comprises a Lugol's iodine. Lugol's iodine, also known as Lugol's solution, first made in 1829, is a solution of elemental iodine and potassium iodide in water, named after the French physician J. G. A. Lugol. Lugol's iodine solution is often used as an antiseptic and disinfectant, for emergency disinfection of drinking water, and as a reagent for starch detection in routine laboratory and medical tests.

It has been used more rarely to replenish iodine deficiency. The inventors found it works well for the application above.

The present invention furthermore, relates to an ultrasonic couplant spray comprising starch, and an antiseptic compound or a pharmaceutical acceptable salt thereof.

The present invention further relates to an ultrasonic couplant spray according to the present invention or a kit according to the present invention for use in sonography. In a preferred embodiment of the present invention the sonography is performed to guide punctures or accesses during interventional or surgical procedures.

The present invention also relates to an imaging method comprising the steps of applying an ultrasonic couplant spray according to claims 16 or 17 or a kit according to any one of claims 13 onto a surface of an object to be imaged and transmitting sound energy through said spray to said surface. Preferably, the object is a part of the body of an individual and the surface is a part of the skin of said body. Preferably, the imaging method is applied in the context of sonography. In one embodiment, veins, particularly varicose veins, are to be imaged.

It will be apparent that the embodiments as described in the description and/or any one of the examples can be independently used and combined with any one of the embodiments described hereinbefore and claimed in the appended claims set. Thus, these and other embodiments are disclosed and encompassed by the description and examples of the present invention.

All experiments were done with patient consent.

FIGURE CAPTIONS

Figure 1:
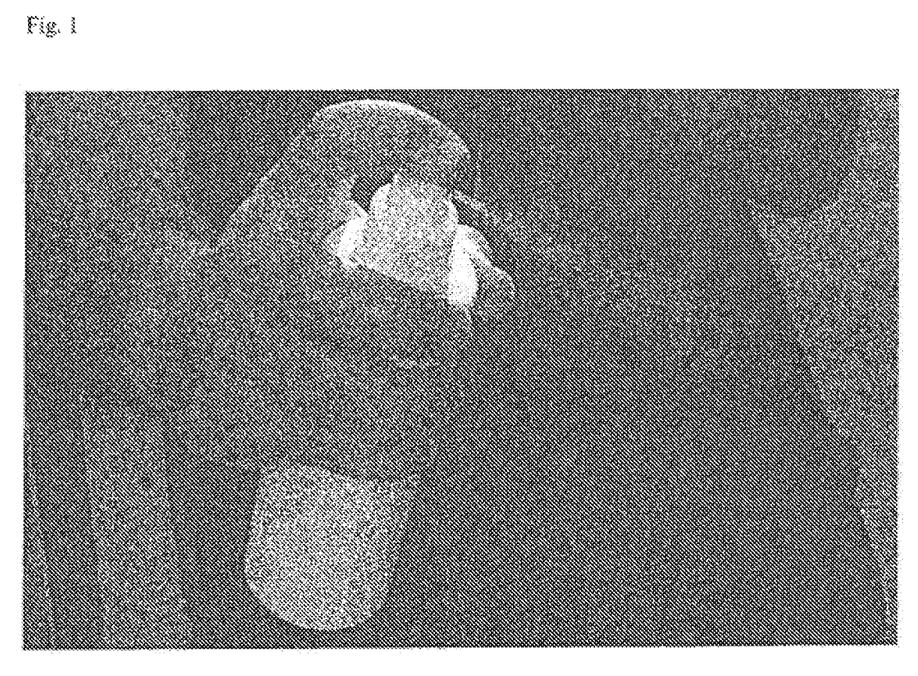

FIG. 1

FIG. 1 shows test series 11, the gel-spray according to the invention without inhalable aerosols.

Figure 2:
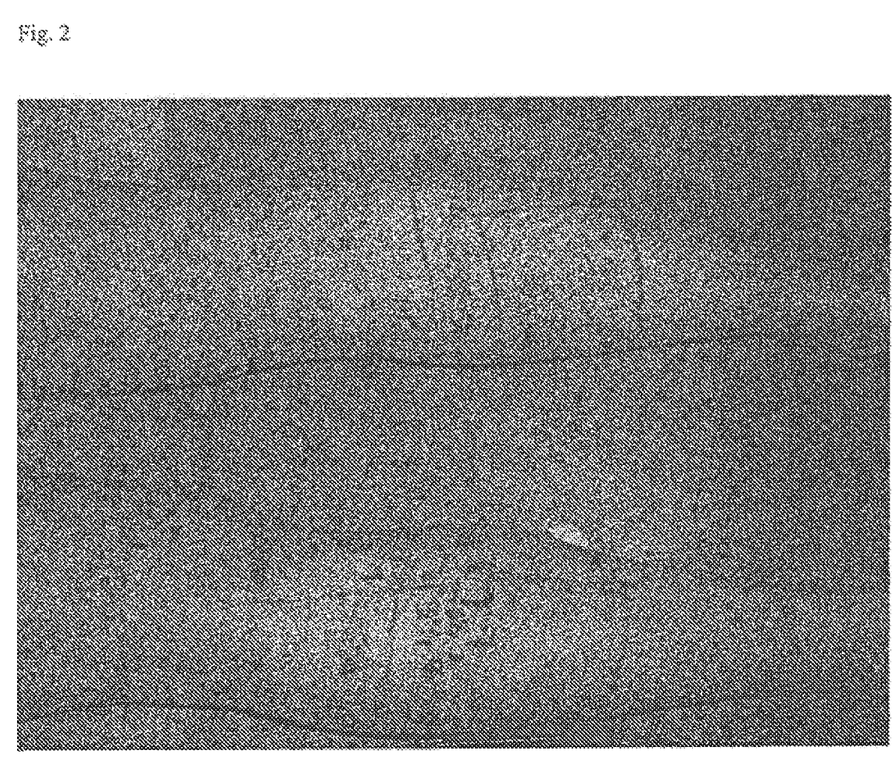

FIG. 2

FIG. 2 shows example test areas of series 11.

Figure 3A:
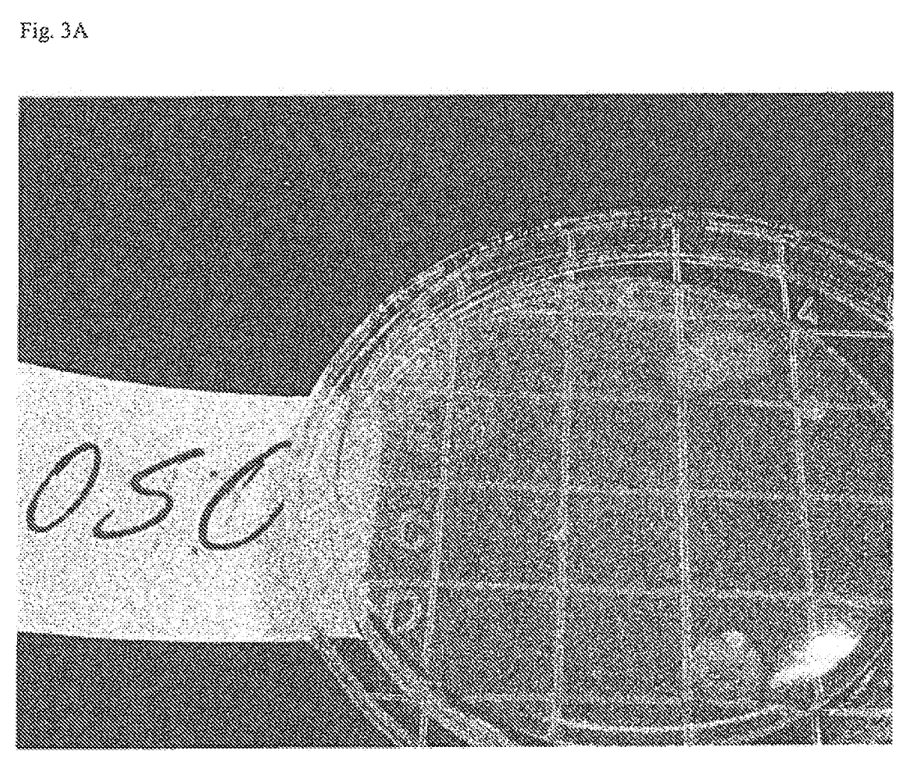
Figure 3B:
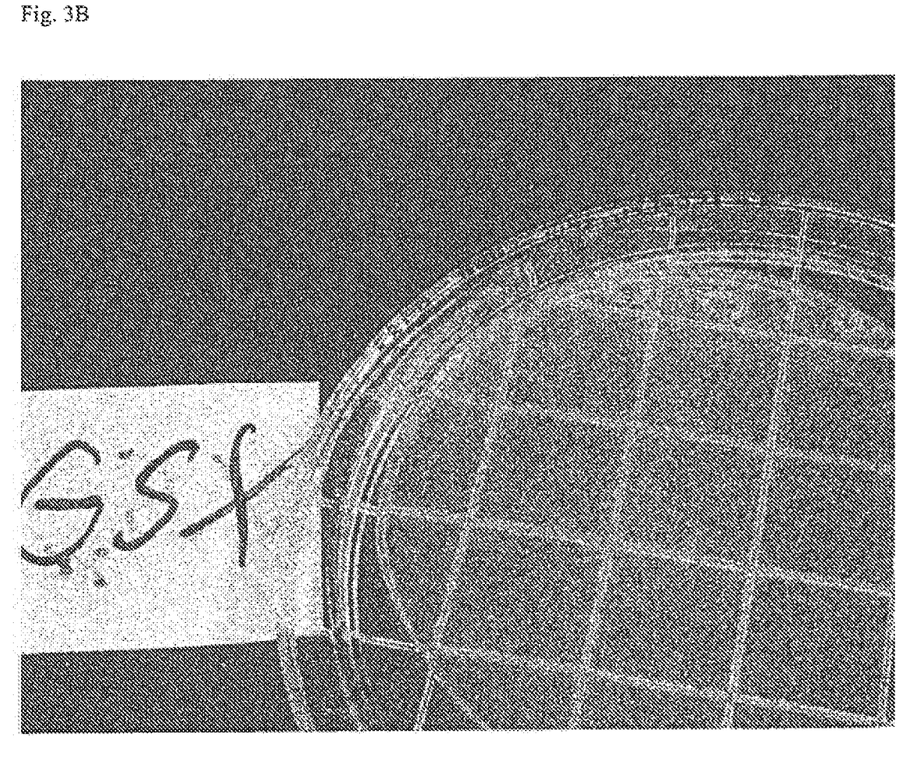

FIGS. 3A and 3B

A) Octeniderm area test with Rodac agar after 48 h breeding: bacteria, funghi

B) Couplant spray according to the invention area test with Rodac agar after 48 h breeding: no growth

Figure 4:
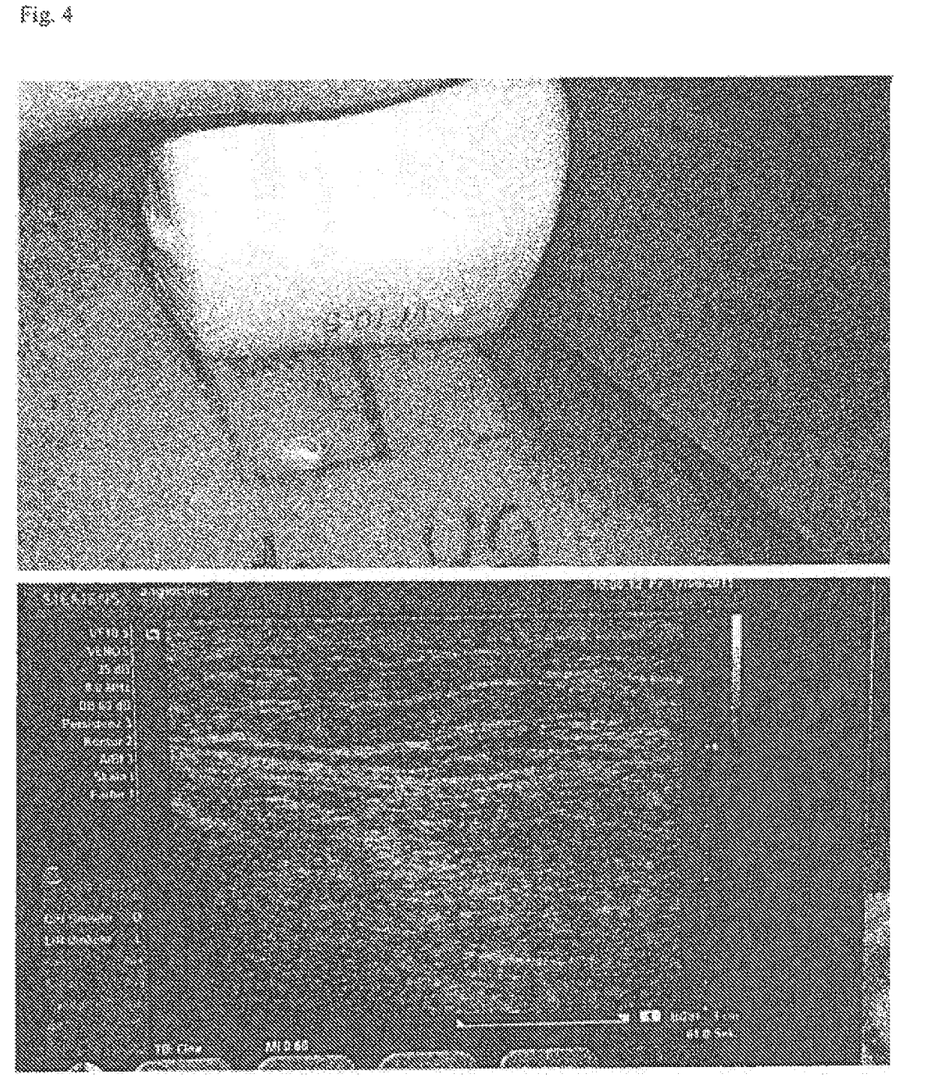

FIG. 4

FIG. 4 shows a comparison of ultrasound images, standard (Aquasonic®, left) versus invention (right): No visible difference is apparent.

EXAMPLES

The spray according to the invention was compared to Octenisept (OS) and Octeniderm (OD) and standard ultrasound gel (Aquasonic® Gel sterile, AQ) in the following first setting (series I). All media were applied and, if still visible, wiped off after 2 minutes. The region was tested with RODAC agar for bacteria and fungi (diameter about 6.5 cm). The region was usually the leg.

| Substance | Amount applied | Region in cm² | Samples | Number of bacteria | Average number of bacteria |
|---|---|---|---|---|---|
| Invention | 1.5 g | 10 × 10 cm | 12 | 0-3 | 0.67 |
| AQ | 4 g | 10 × 10 cm | 12 | 19-250 | 60.16 |
| OD | 1.5 g | 10 × 10 cm | 12 | 0-3 | 1.16 |
| OS | 1.5 g | 10 × 10 cm | 12 | 1-3 | 1.41 |

In another setting (series II), even closer to the general application, standard disinfection with Octeniderm (2×5 spray actions, 2×60 s residence time, wiping off with sterile cloth) was compared to the use of the invention as ultrasound contact medium during the diagnostic preparation before puncture for vascular access. The procedure using the invention consisted of 5 spray actions to cover target area with agent, followed by 2 min, ultrasound action with the ultrasound transducer within the target area, and wiping with sterile cloth. Results: While Octeniderm, as a standard in disinfection, still left bacteria and fungi growing in 1-4 colonies (aerobic sporulating organisms, mold fungus, micrococcus, coagulase negative staphylococcae), the invention left not a single colony growing.

| Substance | Amount applied | Region in cm² | Samples | Number of bacteria/ funghi | Average number of bacteria/ funghi |
|---|---|---|---|---|---|
| Invention | 1.5 g | 10 × 10 cm | 6 | 0 | 0 |
| OD | 1.5 g | 10 × 10 cm | 6 | 0-4 | 1.8 |

The invention claimed is:

1. An imaging method comprising applying an ultrasonic couplant spray onto a surface to be imaged and transmitting sound energy to said surface,
 wherein the ultrasonic couplant spray comprises:
  a starch in an amount of from 6 wt % to 10 wt %, based on the total weight of the spray, wherein the starch is selected from corn starch, rice starch, wheat starch, potato starch, cassava starch, and a modified starch;

an antiseptic compound or a pharmaceutically acceptable salt thereof;
a fatty substance; and
a starch degrading enzyme,
wherein the ultrasonic couplant spray comprises droplets exceeding an average diameter of 50 μm,
wherein the ultrasonic couplant spray does not form an aerosol,
and
wherein the fatty substance and the starch degrading enzyme together prevent the precipitation of the starch.

2. The method of claim 1, wherein the antiseptic compound is bactericidal, fungicidal, and/or virucidal.

3. The method of claim 1, wherein the antiseptic compound is a quaternary ammonium compound.

4. The method of claim 1, wherein the antiseptic compound is selected from octenidin hydrochloride, benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride, and domiphen bromide.

5. The method of claim 1, wherein the composition further comprises:
i) a fast-acting local anesthetic compound or a pharmaceutically acceptable salt thereof, and/or
ii) a local anesthetic compound with long lasting anesthetic effect or a pharmaceutically acceptable salt thereof.

6. The method of claim 5, wherein the fast-acting anesthetic compound and the local anesthetic compound with long lasting anesthetic effect are independently selected from amino amide-type local anesthetic drug, amino ester-type local anesthetic drug, and amino amide ester-type local anesthetic drug.

7. The method of claim 5, wherein the fast-acting anesthetic compound is selected from lidocaine, mepivacaine, prilocaine, articaine, etidocaine, benzocaine, and 2-chlor procaine.

8. A kit comprising a spray device and an ultrasonic couplant spray, wherein the ultrasonic couplant spray comprises:
a starch in an amount of from 6 wt % to 10 wt %, based on the total weight of the spray, wherein the starch is selected from corn starch, rice starch, wheat starch, potato starch, cassava starch, and modified starch;
an antiseptic compound or a pharmaceutically acceptable salt thereof;
a fatty substance; and
a starch degrading enzyme,
wherein the ultrasonic couplant spray comprises droplets exceeding an average diameter of 50 μm,
wherein the ultrasonic couplant does not form an aerosol, and
wherein the fatty substance and the starch degrading enzyme together prevent the precipitation of the starch.

9. The kit according to claim 8, wherein the kit further comprises a device for marking the skin.

10. An ultrasonic couplant spray comprising:
a starch in an amount of from 6 wt % to 10 wt %, based on the total weight of the spray, wherein the starch is selected from corn starch, rice starch, wheat starch, potato starch, cassava starch, and modified starch;
an antiseptic compound or a pharmaceutical acceptable salt thereof;
a fatty substance; and
a starch degrading enzyme,
wherein the ultrasonic couplant spray comprises droplets exceeding an average diameter of 50 μm,
wherein the ultrasonic couplant spray does not form an aerosol, and
wherein the fatty substance and the starch degrading enzyme together prevent the precipitation of the starch.

11. The method of claim 1, wherein the imaging method is performed to catheterize veins and/or arteries, to diagnose obstruction of arteries, to diagnose DVT, and/or to determine extent and severity of venous insufficiency.

12. An imaging method comprising the steps of applying the ultrasonic couplant spray of claim 10 onto a surface to be imaged and transmitting sound energy through said spray to said surface.

13. An imaging method comprising the steps of applying the contents of the kit of claim 8 onto a surface to be imaged and transmitting sound energy through said spray to said surface.

* * * * *